United States Patent
Li et al.

(10) Patent No.: US 6,365,415 B1
(45) Date of Patent: Apr. 2, 2002

(54) METHOD FOR CHARACTERIZATION AND QUALITY CONTROL OF POROUS MEDIA

(75) Inventors: Changming Li; Song Shi; George Maracas, all of Phoenix; Vi-En Choong, Chandler, all of AZ (US)

(73) Assignee: Motorola Inc., Northbrook, IL (US)

( * ) Notice: Subject to any disclaimer, the term of this patent is extended or adjusted under 35 U.S.C. 154(b) by 0 days.

(21) Appl. No.: 09/478,727

(22) Filed: Jan. 6, 2000

(51) Int. Cl.$^7$ ................................................ G01N 1/00
(52) U.S. Cl. ................ 436/174; 436/335; 436/177; 436/178; 436/515; 436/516; 204/456; 204/469; 204/470; 204/546; 204/641
(58) Field of Search ............................... 436/535, 174, 436/177, 178, 515, 516; 204/456, 469, 470, 546, 641

(56) References Cited

U.S. PATENT DOCUMENTS 5,556,756 A * 9/1996 Olsen et al. ................ 435/7.1
5,963,417 A * 10/1999 Anderson et al. ........... 361/503

FOREIGN PATENT DOCUMENTS

| EP | 1 087 036 A | 3/2001 |
| SU | 1 764 818 A | 9/1992 |

* cited by examiner

Primary Examiner—Jill Warden
Assistant Examiner—Monique T. Cole
(74) Attorney, Agent, or Firm—Brinks Hofer Gilson & Lione

(57) ABSTRACT

The present invention provides a method to characterize, optimize, and control the quality and production of hydrogel media. Additionally, the present invention provides a method for determining the size, size distribution, and spatial distribution of the pores of a porous substrate. More particularly, the invention provides a method for determining the size, size distribution, and spatial distribution of the pores of a polymeric hydrogel-based substrate.

29 Claims, 3 Drawing Sheets

METHOD FOR CHARACTERIZATION AND QUALITY CONTROL OF POROUS MEDIA

BACKGROUND OF THE INVENTION

1. Field of the Invention

This invention relates to the fabrication of biochip arrays. In particular, the invention relates to the characterization, optimization, and quality control of bioarrays fabricated from porous media. More particularly, the invention relates to a method for determining the size, size distribution, and spatial distribution of the pores of a porous substrate, and even more particularly, the invention relates to a method for determining the size, size distribution, and spatial distribution of the pores of a polymeric hydrogel-based substrate.

2. Background of the Invention

Microfabricated arrays (biochips) of oligonucleotides, nucleic acids, or peptides have utility in a wide variety of applications, including DNA and RNA sequence analysis, diagnostics of genetic diseases, gene polymorphism studies, analysis of gene expression, and studies of receptor-ligand interactions. In the process of biochip fabrication, large numbers of probe molecules are bound to small, defined regions of a substrate. Glass slides, silicon wafers, or polymeric hydrogels may be used as a biochip substrate, with a two-dimensional or three-dimensional substrate surface utilized for probe attachment. As compared to two-dimensional biochip substrates, three-dimensional substrates offer an advantage of increased sensitivity. This increased sensitivity results from the larger surface area of three-dimensional substrates, allowing for the immobilization of a greater number of probe molecules in a fixed two-dimensional area, and in turn permitting the interaction of a greater number of bound probe molecules with target molecules (biomolecules) in a given sample.

Polymeric hydrogels offer several advantages over both glass and silicon as a substrate material for biochip preparation. One of the primary advantages for using porous hydrogel media over other substrate materials is that the polymeric hydrogel matrix is inherently a three-dimensional porous structure, which eliminates the need to perform lithography and etching to form artificial three-dimensional structures. Yet, while the inherent three-dimensional structure of porous hydrogel media can be advantageous, this structure also creates potential difficulties when porous hydrogel material is used as a substrate in the manufacture of biochip arrays.

The optimization and characterization of substrate structure during the preparation of porous hydrogel media, for example, can be particularly problematic. The size, size distribution, and spatial distribution of the pores in a polymeric hydrogel array are important factors in preparing a suitable three-dimensional biochip substrate. For example, if the pores of the porous hydrogel media are not large enough, reaction efficiency may be adversely affected as biomolecules in a given test sample are prevented or restricted from freely interacting with probe molecules bound to the substrate surface. In the manufacturing of porous hydrogel media, a pore size that is approximately an order of a magnitude larger than the largest biomolecules in the sample is desired. However, no methods for directly determining the characteristics of polymeric hydrogel pores are presently available. This is primarily a result of the physical properties of hydrogel porous media, i.e., that the material is soft and easily collapsible, and thus incompatible with currently-available characterization methods. For example, methods such as scanning electron microscopy (SEM), Atomic Force Microscopy (AFM), and Scanning Tunneling Microscopy (STM) cannot currently be used to characterize the structure of hydrogel porous media during the manufacturing process. Thus, there remains a need in the art for a method to characterize and optimize the structure of porous hydrogel media. Additionally, there is also a need in the art for a method to perform quality control on the structure of porous hydrogel media.

SUMMARY OF THE INVENTION

The invention provides a method for characterizing the structure of porous media, primarily for use in the fabrication of bioarrays. More particularly, the invention provides a method for determining the size, size distribution, and spatial distribution of the pores of a porous substrate, and even more particularly, the invention provides a method for determining the size, size distribution, and spatial distribution of the pores of a polymeric hydrogel-based substrate. This is achieved by depositing metal onto the porous media to produce a mechanically stable matrix, which, in turn, is capable of withstanding characterization by standard methods in the art, such as SEM, AFM, or STM.

The method of the present invention offers several advantages over the prior art. For example, the method permits for the direct characterization of the structure of porous media, more particularly the method permits the direct determination of the size, size distribution, and spatial distribution of the pores of a porous hydrogel substrate. Furthermore, the method is capable of determining the structure of porous hydrogel media in its native state, since no method-induced artifacts are introduced into the media during the process of depositing metal onto the porous media and the process can be performed on porous hydrogel media in its hydrated state.

Specific preferred embodiments of the present invention will become evident from the following more detailed description of certain preferred embodiments and the claims.

DETAILED DESCRIPTION OF THE PREFERRED EMBODIMENTS

Figure 1:
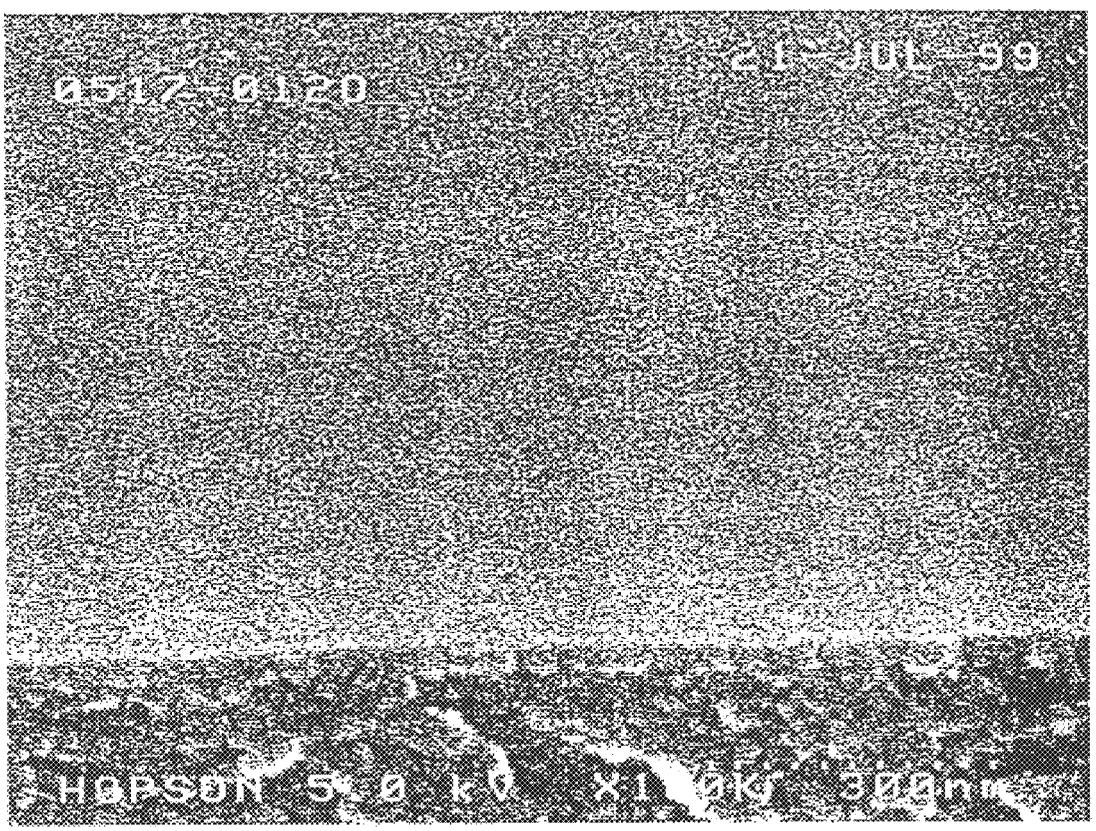
FIG. 1 illustrates a scanning electron micrograph (0–300 nm scale) of a hydrogel array with no plating.

In the method of the present invention, the metal layer may be affixed to the porous media using electroplating or electroless plating techniques. In the preferred embodiment of the present invention, the metal layer is affixed using an electroless plating technique.

The porous media of the present invention may be a conductive or nonconductive polymer. More specifically, the porous media of the present invention may be polyacrylamide gel, polypyrrole, carbon, carbides, oxides, nitrides, or other suitable materials known to those with skill in the art. In the preferred embodiment of the present invention the porous media is a polyacrylamide gel (termed a "hydrogel" herein). The porous hydrogel media of the present invention may be produced using sol-gel, aerogel, or other fabrication techniques known to those with skill in the art.

The porous media of the present invention may be plated, or thermally deposited with metals such as gold, copper, nickel, aluminum and silver. In the preferred embodiment of the present invention, the porous media is plated with gold (Au).

It will be understood by those with skill in the art that the method of the present invention is advantageously practiced on porous hydrogel substrates being used in the commercial production of bioarrays fabricated from porous hydrogel substrates. As used herein, the terms "bioarray," "biochip" and "biochip array" refer to an ordered spatial arrangement of immobilized biomolecules or polymeric anchoring structures on a solid supporting substrate. Preferred probe molecules include nucleic acids, oligonucleotides, peptides, ligands, antibodies and antigens; oligonucleotides are the most preferred probe species.

In one method of the present invention, a quality control determination on a plurality of bioarrays is performed by periodically removing selected porous substrates from a bioarray production run, depositing metal onto the selected porous substrates, examining the structure of the metal-deposited porous substrates, characterizing the structure of the metal-deposited porous substrates, and comparing the structure of the selected porous substrates with a structural standard to determine the quality of the bioarrays being produced in a particular production run. In this manner, an assessment of the manufacturing conditions can be made, thus ensuring that porous substrates having a desired pore size and density are being produce ed. Porous substrates selected for examination using the method of the present invention would be discarded following examination.

The Example that follows is illustrative of specific embodiments of the invention, and various uses thereof. This Example is set forth for explanatory purposes only, and is not to be taken as limiting the invention.

EXAMPLE 1

Electroless Gold Plating of Acrylamide Gel Pad

Polyacrylamide hydrogel arrays were fabricated on glass slides with dimensions of 3 inch by 1 inch. The hydrogel array was photopolymerized on the glass slide using bisacrylamide as cross-linking agent at a final concentration of 5%. The polymerized hydrogel pads had final dimensions of 100 $\mu$m by 100$\mu$m, a thickness of 25 $\mu$m and a pad to pad distance of 300$\mu$m. The size of the complete array was 28 test sites by 28 test sites. Following preparation, the hydrogel arrays were hydrated in water for one hour. During hydration, electroless plating solution (Oremerse Mn, obtained from Technic Inc., Cranston, R.I.), containing 0.25 g/gal. elemental gold, was heated to 65° C. and allowed to stabilize at that temperature in a water bath. Hydrogel arrays were immersed in the plating solution for between 1 minute and 60 minutes. The thickness of the gold plating being applied to the surface of the hydrogel media was controlled by varying the temperature of the water bath and the plating time. The optimum temperature and concentration of the plating metal and length of plating time were selected to minimize artifacts being introduced into the hydrogel porous media. The goal was to select plating conditions in which an accurate representation of the porous hydrogel media in its native state could be obtained, while generating a mechanically stable matrix capable of withstanding characterization by standard methods in the art.

Figure 2:
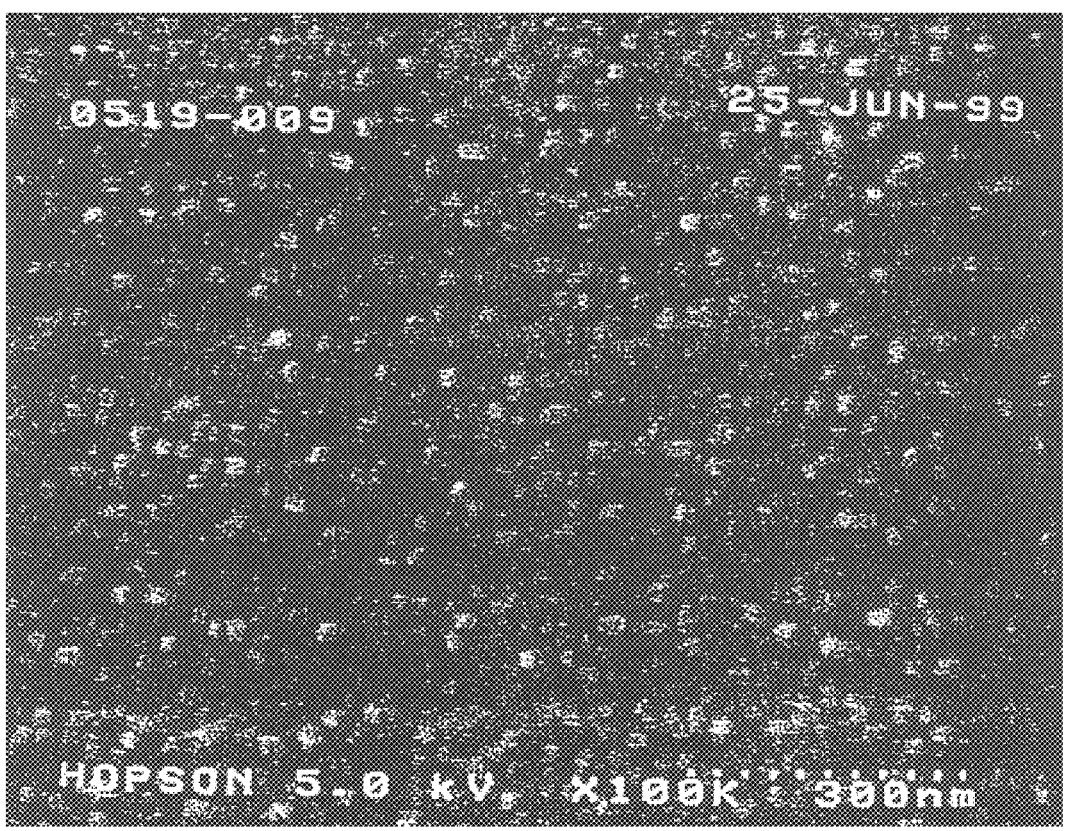
FIG. 2 illustrates a scanning electron micrograph (0–300 nm scale) of a hydrogel array following 1 minute of electroless gold plating.
Figure 3:
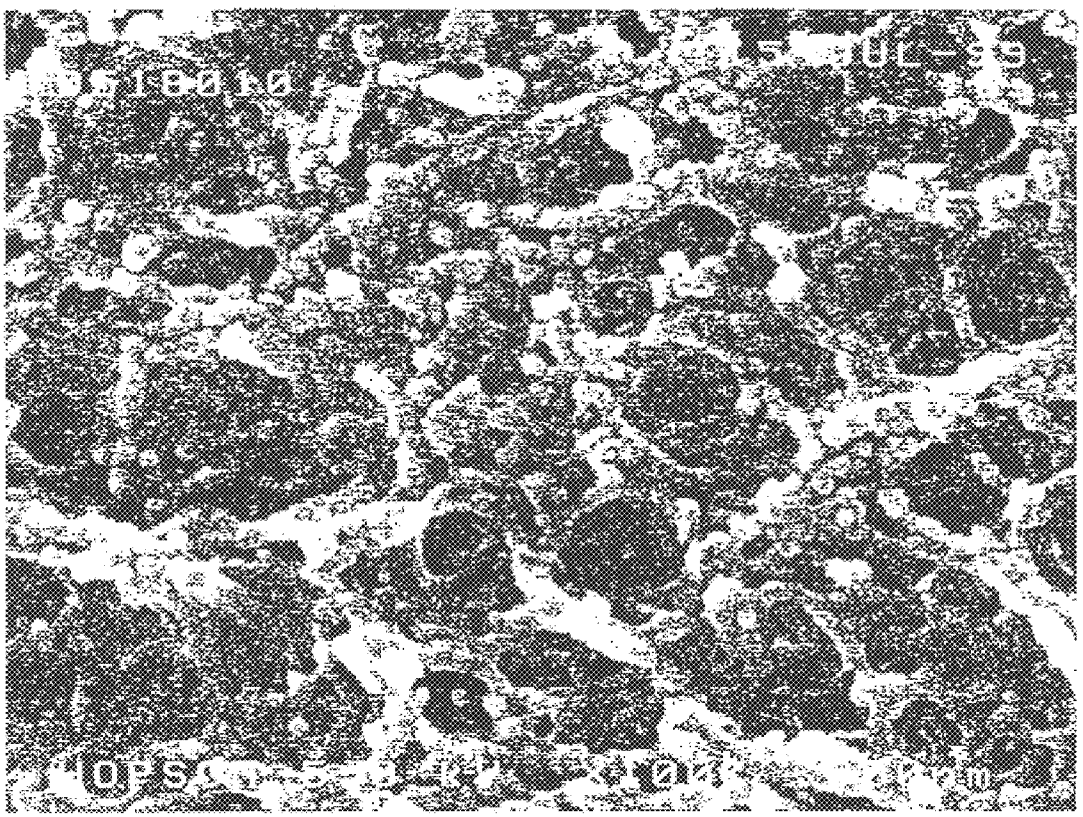
FIG. 3 illustrates a scanning electron micrograph (0–300 nm scale) of a hydrogel array following 40 minutes of electroless gold plating.

Following plating, traces of the plating solution were removed by rinsing the hydrogel arrays in distilled water and allowing the hydrogel arrays to air dry. Plated hydrogel arrays, and unplated controls, were then examined by scanning electron microscopy (SEM). FIG. 1 illustrates a scanning electron micrograph (0–300 nm scale) of an unplated hydrogel array. No distinct structural features can be observed in the unplated control; this result is most likely due to dehydration and collapse of the soft hydrogel media in the vacuum environment required for SEM. FIGS. 2 and 3 illustrate scanning electron micrographs (0–300 nm scale) of a hydrogel array following 1 minute (FIG. 2) and 40 minutes (FIG. 3) of electroless gold plating. Following 1 minute of plating, small gold particles can be observed in the hydrogel array under SEM. However, the size, size distribution, and spatial distribution of pores in the hydrogel media cannot be fully characterized until after at least 40 minutes of plating (shown in FIG. 3). The average pore size for the hydrogel array illustrated in FIG. 3 was determined to be 150 nm.

It should be understood that the foregoing disclosure emphasizes certain specific embodiments of the invention and that all modifications or alternatives equivalent thereto are within the spirit and scope of the invention as set forth in the appended claims.

What we claim is:

1. A method for characterizing the structure of porous media, comprising the steps of:
    (a) depositing elemental mental onto the porous media,
    (b) examining the structure of the metal-deposited porous media with scanning electron microscopy, scanning tunneling microscopy, or atomic force microscopy; and
    (c) characterizing the structure of the porous media by determining thesize,size distribution, or spatial distribution of pores in the porous media.

2. The method of claim 1, wherein the porous media is a polyacrylamide gel.

3. The method of claim 2, wherein the polyacrylamide gel is maintained in a hydrated state while the metal is deposited.

4. The method of claim 1, wherein the elemental metal is deposited onto the porous media by electroplating.

5. The method of claim 1, wherein the elemental metal is deposited onto the porous media by electroless plating.

6. The method of claim 1, wherein the elemental metal is gold, silver, nickel, aluminum, or copper.

7. The method of claim 6, wherein the elemental metal is gold.

8. A method for performing a quality control determination on a plurality of arrays comprising a porous media deposited on a solid substrate, comprising the steps of:
    (a) depositing an elemental metal onto the porous media,
    (b) examining the structure of the metal-deposited porous media with scannig elementron microsopy scanning tunneling microscopy, or aatomic microscopy;
    (c) characterizing the structure of the porous media by determining the size, size distribution, or spatial distribution of pores in the porous media; and
    (d) comparing the structure of the porous media characterized in step (c) with a structural standard, whereby the quality of the arrays is determined thereby.

9. The method of claim 8, wherein the porous media is a polyacrylamide gel.

10. The method of claim 8, wherein the elemental metal is deposited onto the porous media by electroplating.

11. The method of claim 8, wherein the elemental metal is deposited onto the porous media by electroless plating.

12. The method of claim 8, wherein the elemental metal is gold, silver, nickel, aluminum, or copper.

13. The method of claim 12, wherein the elemental metal is gold.

14. A method for characterizing the structure of a hydrogel, comprising the steps of:
  (a) depositing an elemental metal onto the hydrogel by electroplating or electroless plating, wherein a mechanically stable matrix wiht scanning electron microscopy, scanning tunneling microscopy, or atomic force results;
  (b) examining the structure of the mechanically stable matrix; and
  (c) characterizing the structure of the hydrogel by determining the size, size distribution, or spatial distribution of pores in the hydrogen.

15. The method of claim 14, wherein the hydrogel is selected from the group consisting of polypyrrole, carbon, carbides, oxides, nitrides, and polyacrylamide gel.

16. The method of claim 14, wherein the hydrogel is selected from the group consisting of polypyrrole and polyacrylamide gel.

17. The method of claim 14, wherein the hydrogel is a polyacrylamide gel.

18. The method of claim 14, wherein the hydrogel is maintained in a hydrated state while the metal is deposited.

19. The method of claim 14, wherein electroless plating continues for at least 40 minutes.

20. The method of claim 14, wherein the elemental metal is gold, silver, nickel, aluminum, copper, or mixtures thereof.

21. The method of claim 14, wherein the elemental metal is gold.

22. The method of claim 14, wherein the hydrogel is photopolymerized onto a solid substrate using a cross-linking agent.

23. The method of claim 22, wherein the solid substrate is glass.

24. The method of claim 22, wherein the cross-linking agent is bisacrylamide.

25. A method for performing a quality control determination on a plurality of arrays comprising a hydrogel deposited on a solid substrate, comprising the steps of:
  (a) depositing an elemental metal onto the hydrogel by electroplating or electroless plating;
  (b) examining the structure of the metal-deposited hydrogel with scanning electron microscopy, scanning tunneling microscopy, or atomic force microscopy;
  (c) characterizing the structure of the hydrogel by determining the size, size distribution, or spatial distribution of pores in the hydrogel; and
  (d) comparing the structure of the hydrogel characterized in step (c) with a structural standard, whereby the quality of the arrays is determined.

26. The method of claim 25, wherein the hydrogel is a polyacrylamide gel.

27. The method of claim 25, wherein the elemental metal is deposited onto the hydrogel by electroless plating.

28. The method of claim 25, wherein the elemental metal is gold, silver, nickel, aluminum, copper, or mixtures thereof.

29. The method of claim 25, wherein the elemental metal is gold.

* * * * *

UNITED STATES PATENT AND TRADEMARK OFFICE
CERTIFICATE OF CORRECTION

PATENT NO.    : 6,365,415 B1
DATED         : April 2, 2002
INVENTOR(S)   : Changming Li et al.

It is certified that error appears in the above-identified patent and that said Letters Patent is hereby corrected as shown below:

Column 4,
Line 30, delete "thesize,size" and substitute -- the size, size -- in its place.
Line 50, delete "scanning elementron microscopy scanning" and substitute -- scanning electron microscopy, scanning -- in its place.
Line 51, delete "aatomic" and substitute -- atomic force -- in its place.

Column 5,
Line 5, delete "wiht" and substitute -- with -- in its place.

Signed and Sealed this

Eleventh Day of March, 2003

JAMES E. ROGAN
*Director of the United States Patent and Trademark Office*